United States Patent [19]

Takatsu

[11] Patent Number: 4,795,346
[45] Date of Patent: Jan. 3, 1989

[54] VISUAL MEASUREMENT METHOD FOR READING OCCULUSAL CLEARANCE

[75] Inventor: Toshio Takatsu, No. 7-2-504, Tsudanuma 2-chome, Narashino-shi, Chiba-ken, Japan

[73] Assignees: Toshio Takatsu, Narashino; G-C Dental Industrial Corp., Tokyo, both of Japan

[21] Appl. No.: 64,394

[22] Filed: Jun. 22, 1987

[30] Foreign Application Priority Data

Jul. 16, 1986 [JP] Japan .................. 61-165594

[51] Int. Cl.⁴ .............................. A61C 5/00
[52] U.S. Cl. ..................... 433/215; 433/75; 433/141; 33/169 B; 33/573
[58] Field of Search ............ 433/71, 72, 75, 141, 433/214, 215, 216; 33/169 B, 169 F, 513, 514

[56] References Cited

U.S. PATENT DOCUMENTS

| | | | |
|---|---|---|---|
| 3,935,640 | 2/1976 | Cohan | 433/75 |
| 4,275,672 | 6/1981 | Clad | 33/169 B |
| 4,552,531 | 11/1985 | Martin | 433/141 |
| 4,677,756 | 7/1987 | Simon et al. | 33/514 |

FOREIGN PATENT DOCUMENTS 615339 1/1980 Switzerland ............ 433/141

*Primary Examiner*—Samuel Scott
*Assistant Examiner*—Noah Kamen
*Attorney, Agent, or Firm*—Oblon, Fisher, Spivak, McClelland & Maier

[57] ABSTRACT

In the visual measurement system for reading the occulusal clearance between the pulpal cavity wall and the opposing tooth, a thermoplastic material for occulusal registration is cast in a pulpal cavity wall at the time of the primary preparation of a cavity or abutment, and is put into occulusal closure engagement with the opposing tooth to register the opposing tooth surface thereon, the material being capable of being softened and formed at a temperature slightly higher than the internal temperature of the oral cavity and being of slight transparency. A specially designed explorer for thickness mesurement is then inserted into the required regions on the prepared surface covered with the material, thereby to produce indentations which are of various sizes and shapes similar to those of the head of the explorer, and which has its width coincident with the indented depth, and the sizes of the indentations are visually observed to read the clearance between the pulpal cavity wall and the opposing tooth.

2 Claims, 5 Drawing Sheets (a) (b)

VISUAL MEASUREMENT METHOD FOR READING OCCULUSAL CLEARANCE

BACKGROUND OF THE INVENTION

1. Field of the Invention

The present invention relates to a checking method to be effected at the time of cavity preparation of full crown preparation that is the first stage of the restoration of tooth decay, especially posterior tooth decay and, more particularly, a method for objectively, readily and quantitatively measuring and reading the occulusal clearance between the pulpal cavity wall and the opposing tooth without recourse to the conventional method relying upon the sixth sense, thereby determining the proper occulusal clearance for the purpose of achieving the reliability and perpetuity of restoration and securing the preservation of tooth substances.

2. Statement of the Prior Art

Hitherto, the determination of the occulusal clearance has been made (1) by forming a guide groove within tooth substances and comparing the depth and thickness thereof with the length and diameter of a reference bar or point, or (2) allowing a softened paraffin wax plate to be bit upon and seeing through the thus bit portion under the illumination of light.

However, the first method comes short of expectation, and is unreliable, partly because unexpected regions are deficient in the amount of reduction. The second checking method is most widely used owing to its simplified operation and no need of using any special tool and material, but has the grave disadvantages, as mentioned in the following, which render it unreliable. Typically, those disadvantages are:

(A) Since the occulusion registered surface is in the negative form, it is hard to comprehend the whole thereof in three dimensions, when observing it outside of the mouth. Hence, it is very difficult to properly specify the regions to be restored, if any.

(B) At the time of occulusal closure, the impression itself undergoes deformation due to the deformation-due-to-flow, stress-on-removing and sticking of paraffin wax, which tends to give rise to a variation in the thickness of the wax of the associated region.

(C) The thickness of the occulusal clearance, i.e., the occulusal paraffin wax is presumed by comparison of relative transparency, and is thus very inaccurate, since it cannot be measured and determined on a quantitative basis.

The tooth substances should be properly reduced. In most cases, the posterior tooth decay (mainly due to dental cavities) of molars exposed to a strong mastication force is generally restored by a metal casting. In order to allow such a casting to stand up to the mastication force and fulfill its function over an extended period of time without any fall-off or damage and causing damage to the teeth per se, a variety of requirements are necessary, when preparing and reducing the teeth for receiving it. Of particular importance is the retention form. In the case of an internal casting (inlay), its retention is achieved by the surrounding cavity wall. In this case, it is required that the cavity floor be located as uniformly as possible and at a depth of about 0.5 to 1.0 mm in dentine. However, although conceptually feasible, to keep the cavity floor depth constant is actually more difficult than expected in clinical practice. In effect, such uncomfortable incidents as referred to below often occur by improper reduction.

I. Referring to the case where the clearance between the prepared surface and the opposite tooth is excessively insufficient, even the occulusal surface of the casting may be perforated at the time of occulusal adjustment during try-in of the casting. This is particularly disadvantageous to both patient and dentist in that the same procedure had to be commenced again from the re-preparation of teeth. Even when such perforation does not fortunately take place, the occulusal surface may locally become thin to an extreme degree. That thinned portion may eventually come to be perforated. Alternatively, stress concentration from mastication may take place in such a region, thus giving rise to the deformation of the casting. In some cases, the restoration casting may fall off due to the dislodgement of the luting material.

II. Referring to the case wherein the clearance between the prepared surface and the opposite tooth is excessive, excessive reduction of tooth substances causes damage to the dental pulp or weakening of the teeth, thus leading to a possibility of the tooth fracture.

As detailed above, the reasons for the "deficiency" or "excessiveness" of the clearance are considered to be due to lack of examination of its size, or owing to the fact that, although examined, any proper checking or determination of its size is almost impossible in the existing method.

III. Referring to the case where the clearance between the prepared surface and the opposite tooth is properly set, the thorough functions of the teeth nad restorations are expected to remain permanent. In most cases, however, the determination of the clearance relies upon the sixth sense, although properly achieved. Thus, proper clearence, even if it may be achieved, is far from reassuring, since its result differs from person to person and is poor in reproducibility.

With a view to eliminating the disadvantages of the aforesaid occulusal register methods with wax plates, Harumi Kurita proposed the method, as mentioned in the following (see "Inlay", edited by Kenji Marumori, pp. 67-71; published from ISHIYAKU SHUPPAN, Tokyo 1980). More exactly, Kurita prepared a scale by arranging a series of blue wax blocks having incrementally varying thicknesses. Then, Kurita observed a cavity depth in the thus obtained occulusion registered wax under the transmission of light, while comparing the cavity depth with the scale. However, since the occulusion registration is also in the negative form in this method, it still remains hard to specify the regions without making any modification thereto. Further, this method offers some problems hard to solve in that comparison in color with the scale is troublesome, considerable skill is required for proper determination, and so on.

SUMMARY OF THE INVENTION

In order to obviate the foregoing disadvantages the prior art has, the present inventor has invented a clearance measuring method using a combination of a thermoplastic material for occulusal registration (hereinafter often referred to as the registering material) with a specially designed explorer for thickness measurement (hereinafter often referred to as the measuring explorer). With the method according to the present invention, it is feasible to read accurately, readily, momentarily and quantitatively the amount of clearances in every portion of the prepared surface of the tooth at any time. In consequence, it is possible to reduce to the minimum the required amount of the tooth substances and, at the same time, determine the proper clearance, whereby the restoration and the tooth restored thereby are expected to fulfill their own functions. Thus, the present invention has succeeded in the provision of a visual measurement system for reading the clearance, which can solve all the foregoing problems of the prior art.

According to the present invention, there is provided a method for directly measuring the amount of the clearance by the combination of a material for occulusal registration with a specially designed explorer for thickness measurement. When applied to the restoration by inlays, the material and tool according to the present invention may be used in the following manner.

According to the present invention, the material for occulusal registration is required to have the following manipulative properties:

(1) Its thermoplasticity should be such that it is softened at a temperature slightly higher than that prevailing in the oral cavity, and can readily be formed at that temperature.

(2) It should possess a proper degree of body (consistency) and a proper degree of plasticity at the temperature prevailing in the oral cavity.

(3) It should show a proper degree of stickiness with respect to the tooth substances and, (4) The shallow portion in the cavity floor and the cavity margin should be of slightly noticeable transparency.

Thus, the material according to the present invention is required to be formed of a thermoplastic resin material which can readily be formed at a temperature slightly higher than that prevailing in the oral cavity and a certain degree of body at such temperature.

BRIEF DESCRIPTION OF THE DRAWINGS

How to use such a material for occulusal registration will be explained with reference to the accompanying drawings, in which

FIGS. 1 to 6 are occulusal views each showing the procedures of the present system, when applied to the preparation of the class I inlay cavity in the upper first molar, FIGS. 7 to 12 are presented for additionally illustrating FIGS. 1 to 6, and views on the bucco-lingual section surface through the cavity center in the upper first molar, FIGS. 13 to 16 are sectional illustrations, as viewed on the bucco-lingual section, of the present system, when applied to the full crown preparation in the molar, FIGS. 17 to 20 are sectional illustrations, as viewed on the bucco-lingual section, of the procedures of the present system, when applied to the preparation of the occulusal amalgam cavity, FIGS. 21 to 24 are sectional illustrations, as viewed on the bucco-lingual section, of the procedures of the present system, when applied to the preparation of the occulusal composite resin cavity.

DETAILED DESCRIPTION OF THE DRAWINGS

Figure 1:
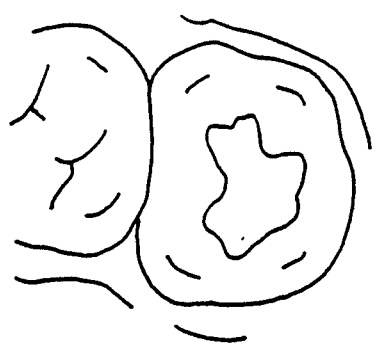
FIGS. 1 to 24 illustrate the procedures of the cavity preparation according to the present invention.
Figure 4:
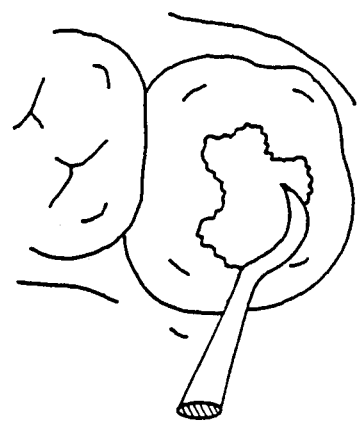
Figure 2:
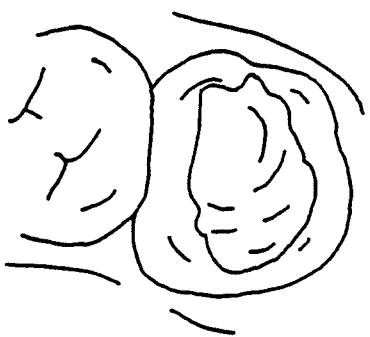
Figure 5:
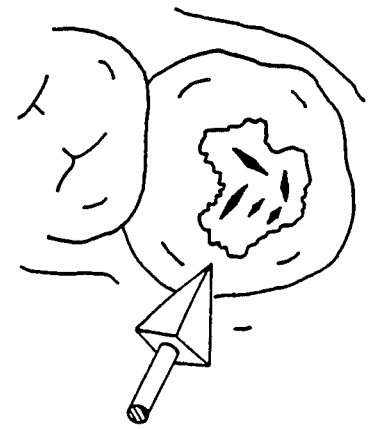
Figure 3:
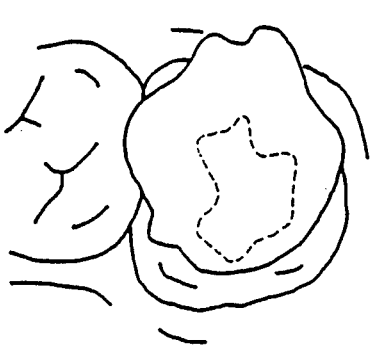
Figure 25:
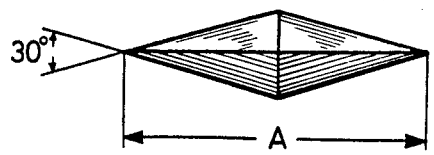
FIG. 25 shows the head of the measuring explorer, wherein a is a plane view, and b, a front view.
Figure 25:
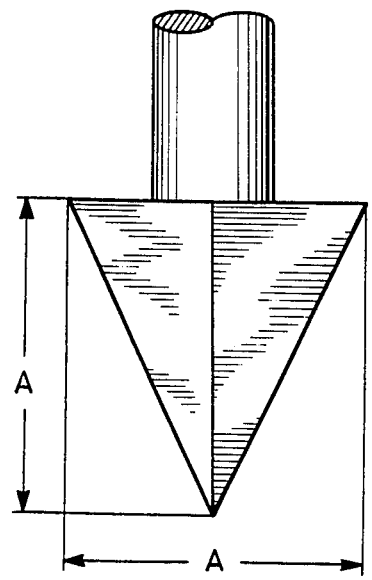

A material having the aforesaid manipulative properties is loaded in a suitable syringe, which is heated over a gas burner to heat and soften. In this manner, it is cast up (FIG. 2) in such a manner that it overflows slightly into a primarily prepared cavity (FIG. 1). Immediately afterwards, instructions for occulusal closure are given to a patient, and the material for occulusal registration is cooled down to the internal temperature of the oral cavity and hardened for a waiting time of about 10 seconds. Upon occulusal opening, it is found that the opposing tooth surface is registered on the material for occulusal registration on the cavity (FIG. 3). Usually, the material for occulusal registration overflows from the cavity margin at this time. Since the material according to the present invention has a certain degree of transparency, however, the location of the cavity margin is well confirmed so that the overflowing portion can easily be judged. That overflowing portion is then removed by a heated carver (FIG. 4). The head of the measuring explorer, as shown in FIG. 25, is inserted into the required regions on the occulusion registered surface (FIG. 5).

Figure 6:
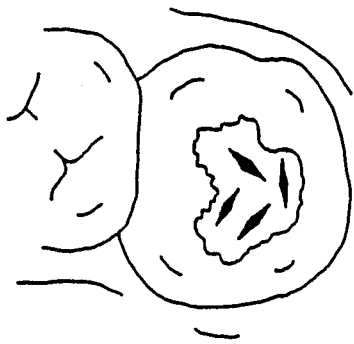

The explorer used in the present invention is characterized by the form of its head, which is rhombic in cross-section. The explorer is designed in such a manner that when its head is vertically inserted down into the registration material by a mm, the longitudinal axis diameter of the resulting rhombic indentation is correspondingly a mm. Accordingly, to read the width of the longitudinal axis diameter renders it possible to visually determine the size of the clearance in that position in quantitative terms (FIG. 5). If the deficiency or ununiformity of the cavity depth is found by inserting of the explorer and reading of the indentation width, then the registering material is removed from within the cavity to reduce the corresponding portion for correction. In this case, since the registered surface is in the positive form, it is possible to specify that region without dislocating positional relations, as viewed either vertically or horizontally. It is even possible to specify that region with the memory of the registered material prior to its removal, but without causing any variation. To make further assurance, the explorer's head may be applied with marking ink, and then re-inserted into the indentation to record its position on the cavity floor. By way of precaution, the foregoing procedures are repeated after the completion of additional reduction to check whether or not the clearance is correct (FIG. 6). Satisfactory results will come to the completion of cavity preparation.

Although the head of the foregoing explorer illustrated is in the rhombic form, it may be a mere cone having a similar apex (of about 53°), i.e. another shape having a width dimension proportional to the distance of the width dimension from the tip of the head. It is to be noted, however, that an explorer having a conical head is disadvantageous in that its head may contact the surrounding cavity wall and interfere with the measurement of a narrow region. In this regard, the explorer having a rhombic head is easier to handle, since such interference is rather avoidable. If the material for occulusal registration has a certain degree of elasticity, the indentation width is then somewhat smaller than achieved actually under the influence thereof. In this case, however, the conical indentation is more largely affected than the rhombic indentation. In other words, the rhombic indentation is advantageous over conical one in that its size can more precisely be reproduced.

EXAMPLES

On an experimental basis, the tool and material accommodative to the present system were made. They were then applied to the cavity preparation, and a wax pattern was formed in the thus obtained stone model, from which pattern the sectional samples were prepared for observation. The effectiveness of the present system was confirmed from the observed fact that the cavity floor was located at the proper position and the wax pattern was uniform in thickness.

Further and additional explanation will now be made with reference to the drawings.

FIGS. 1 to 6 are occulusal views each showing the procedures of the present system, when applied to the preparation of the class I inlay cavity in the upper first molar. FIG. 1 is a plan view illustrating the primary cavity preparation following the cavities removal, FIG. 2, a plan view illustrating the material for occulusal registration which is heated and softened, and is then cast up in the primarily prepared cavity, and FIG. 3, a plan view which shows the material for occulusal registration, which is put into occulusal closure engagement with the opposite tooth to register the opposite tooth surface thereon, and in which the cavity margin can see through the thined material for occulusal registration. FIG. 4 is a plan view of a portion of the registering material which overflows from within the cavity and is removed by means of a heated carver, and FIG. 5, a plan view which shows the head of the measuring explorer inserted into the required regions on the registering material, and in which the indentations of various sizes are found with a smaller indentation showing that the cavity is still too shallow. FIG. 6 is a plan view showing the indentations which are provided for rechecking after the additional reduction of the cavity, and are found to be substantially uniform in size. This indicates that the cavity floor depth is substantially uniform at any place. Subsequent removal of the registering material and preparation of the marginal bevel leads to the completion of the cavity.

Figure 7:
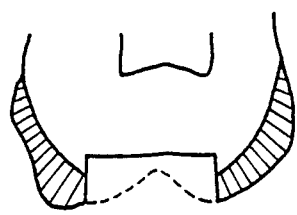
Figure 8:
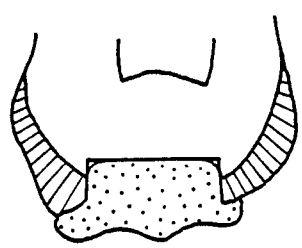
Figure 9:
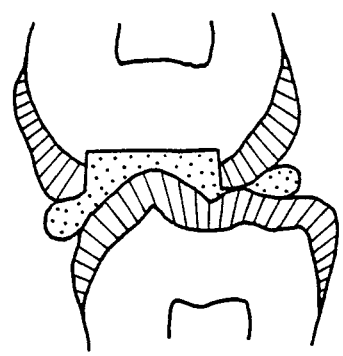
Figure 10:
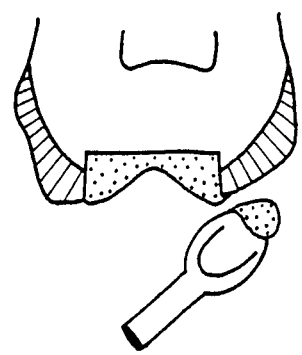
Figure 11:
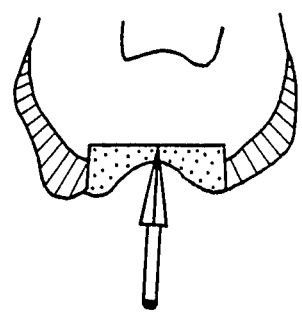
Figure 12:
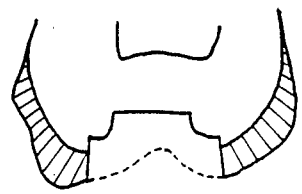

FIGS. 7 to 12 are sectional views for additionally illustrating FIGS. 1 to 6 and on the bucco-lingual section surface through the cavity center in the upper first molar. FIGS. 7 to 12 are similar in the contents to FIGS. 1 to 6. More exactly, FIG. 7 is a sectional view of the primarily prepared cavity, FIG. 8 a sectional view showing the registering material cast on in the cavity, FIG. 9 a sectional view illustrating the occulusal registration carried out while the registering material is put in occulusal closure engagement with the opposing tooth, FIG. 10 a sectional view illustrating an excessive overflowing portion of the registering material, which is removed, FIG. 11 a sectional view showing the respective portions of the registering material which are examined in respect of thickness by means of the measuring explorer, and FIG. 12 a sectional view showing the cavity having its floor reduced due to its excessively shallow floor depth. In this figure, a slight step is shown to be provided on the cavity floor so as to make the cavity depth uniform, while keeping the tooth substances saved. Such a step is useful for the stabilized retention of the inlay.

Figure 13:
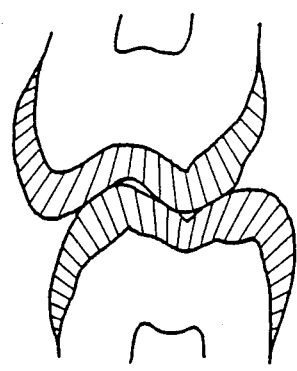
Figure 16:
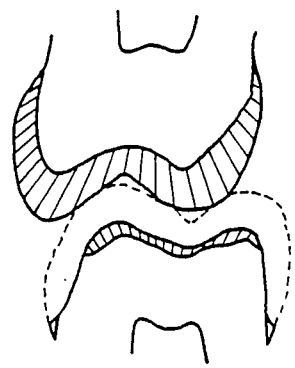
Figure 14:
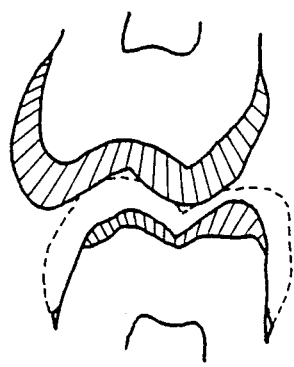
Figure 15:
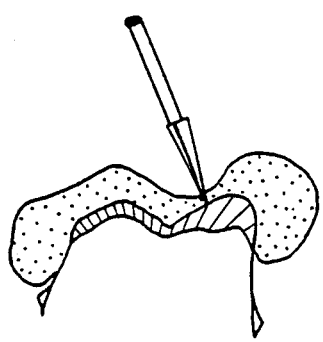
Figure 18:
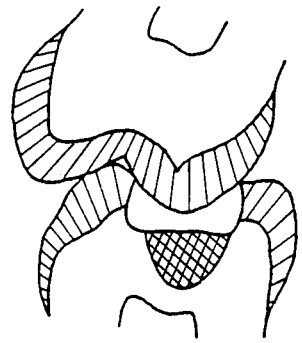
Figure 19:
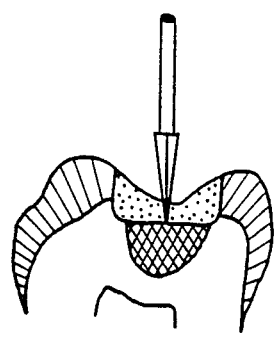
Figure 22:
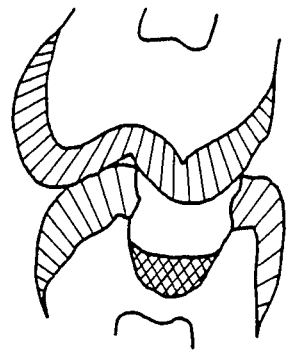

FIGS. 13 to 16 show the examples of the present system applied to the full crown preparation in the molar (e.g., abutment of the bridge). FIG. 13 is a sectional view of the upper and lower molars during occulusion, and FIG. 14 is a sectional view of the primarily prepared lower molar, which shows that the reduction of the internal slope of the lingual cusp is still insufficient. This is a region often tending to undergo "under-reduction" or "over-reduction" since it is hard to observe visually from the buccal side. It is to be noted that, in FIG. 14, a dotted line stands for the contour of the original tooth which has already been reduced. FIG. 15 is a sectional view of the registering material (indicated by scattered points) on which the opposing tooth surface is registered to examine with the measuring explorer the thickness of the registering material around the region into which the lingual cusp of the opposite tooth bites deeply, and FIG. 16 a sectional view of the region having an insufficient clearance, which is reduced, and in which a suitable and vitually uniform clearance is defined between the pulpal cavity wall and the opposing tooth.

Figure 17:
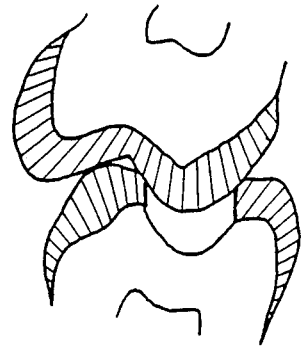
Figure 20:
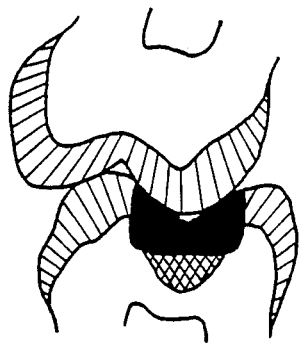
Figure 23:
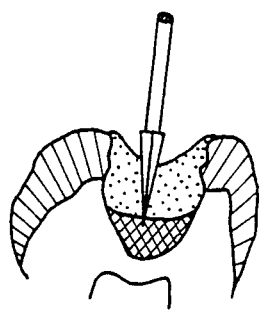

FIGS. 17 to 20 illustrate the examples of the present system applied to the preparation of the occulusal amalgam cavity. FIG. 17 is a sectional view of the lower molar having a carious cavity of a considerably large size, FIG. 18 a sectional view of the primary cavity prepared after filling cement in the deep region left by the removal of dental caries, as hatched, and FIG. 19 a sectional view of the registering material (indicated by scattered points) on which the opposing tooth surface is registered to examine with the measuring explorer the thickness of the registering material around the region into which the lingual cusp of the opposite tooth bites deeply. In the latter example, the cavity floor is still too shallow. FIG. 20 is a sectional view of the example wherein the cavity floor is further reduced to give a suitable clearance and thereby complete the cavity which is in turn restored by an amalgam (indicated by a solid portion). In this example, since the amalgam portion has a suitable thickness, it is very unlikely that it may break upon receiving a strong mastication force.

Figure 21:
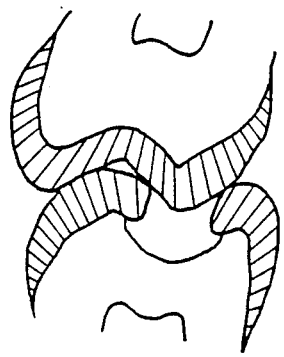
Figure 24:
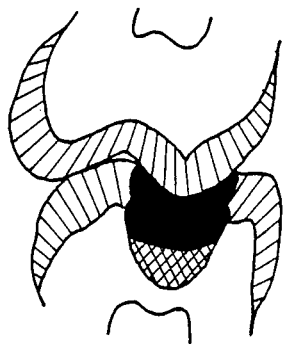

FIGS. 21 to 24 illustrates the examples of the present invention applied to the preparation of the occulusal composite resin cavity. FIG. 21 is a sectional view of the lower molar having a carious cavity of a considerably large size, FIG. 22, a sectional view of the primary cavity prepared after filling cement in the deep region left by the removal of dental caries, as hatched, and FIG. 23, a sectional view of the registering material (indicated by scattered points) on which the opposing tooth surface is registered to examine with the measuring explorer the thickness of the registering material around the region into which the lingual cusp of the opposite tooth bites deeply. In this example, the cavity depth is on the suitable order; however, of importance is to known in advance that cavity depth partly for the purpose of setting the required light-irradiation time, since the material used is a photopolymerization type composite resin. FIG. 24 is a sectional view of the example in which, based on the thickness measurement of the completed photopolymerization type composite resin restoration (indicated by a solid portion), the restoration floor is irradiated with light only for the time period required for its sufficient polymerization and curing.

FIG. 25 shows the head of the explorer for measuring the clearance between the pulpal cavity wall and the opposing tooth, FIG. 25-a being a plan view showing the explorer having a rhombic head and FIG. 25-b, a front view of the same wherein the length of the upper side of the head coincides with the height thereof. Suitably, A is about 3 to 5 mm.

The system according to the present invention is designed to be most frequently applied to the preparation of cavities and abutments in the case of the casting restoration, but may also be effectively used for checking of clearances at the time of preparing cavities for amalgam and posterior composite resins. Hitherto, the cavities for amalgams and composite resins were hardly checked carefully in respect of depth, and were filled as such in most cases. For that reasons, there were accidents such as restoration breakage due to its reduced thickness or pulp irritation due to excessively deep cavities. The checking method involving the system according to the present invention can be applied to the cavities obtained irrespective of the procedures applied, whereby the preservation of tooth substances and the reinforcement of restorations can be achieved in a simple and easy manner. Furthermore, by knowing quantitatively the clearance between the pulpal cavity wall and the opposing tooth at any time, it is possible to properly prepare the tooth surfaces depending upon the characteristics of the restorations of every type including castings, amalgams and composite resins and thereby minimize the reduction of tooth substances and help the restorations to well function permanently.

What is claimed is:

1. A visual measurement process for reading the occulusal clearance between the pulpal cavity wall and the opposing tooth, comprising the steps of:
   casting a heat softened thermoplastic material having transparent properties for occulusal registration in a pulpal cavity wall at the time of the primary preparation of a cavity,
   putting the thermoplastic material in the pulpal cavity wall into occulusal closure engagement with an opposing tooth to register the opposing tooth surface thereon,
   inserting the head of an explorer into selected regions of said thermoplastic material, said head having a shape such that a width dimension thereof increases proportionally to a distance of said width dimension from a tip of said head, thereby to produce indentations which are of various sizes and shapes similar to those of the head of said explorer, and which have widths proportional to the indented depth, and
   visually observing the sizes of said indentations to read the clearance between the pulpal cavity wall and the opposing tooth.

2. The process of claim 1 wherein said explorer head is rhombic.

* * * * *